(12) United States Patent
Draghia-Akli et al.

(10) Patent No.: US 11,453,855 B2
(45) Date of Patent: Sep. 27, 2022

(54) COMPOSITIONS COMPRISING HIGH CONCENTRATION OF BIOLOGICALLY ACTIVE MOLECULES AND PROCESSES FOR PREPARING THE SAME

(71) Applicant: VGXI, INC., The Woodlands, TX (US)

(72) Inventors: Ruxandra Draghia-Akli, Houston, TX (US); Henry Hebel, The Woodlands, TX (US); Ying Cai, The Woodlands, TX (US)

(73) Assignee: VGXI, INC., The Woodlands, TX (US)

( * ) Notice: Subject to any disclaimer, the term of this patent is extended or adjusted under 35 U.S.C. 154(b) by 339 days.

(21) Appl. No.: 16/517,985

(22) Filed: Jul. 22, 2019

(65) Prior Publication Data
US 2020/0017819 A1 Jan. 16, 2020

Related U.S. Application Data

(62) Division of application No. 12/126,611, filed on May 23, 2008, now abandoned.

(60) Provisional application No. 60/939,792, filed on May 23, 2007.

(51) Int. Cl.
*C12N 1/06* (2006.01)
*C12N 15/10* (2006.01)

(52) U.S. Cl.
CPC ........... *C12N 1/06* (2013.01); *C12N 15/1017* (2013.01)

(58) Field of Classification Search
CPC ......... C12N 1/06; C12N 1/066; C12N 15/101
See application file for complete search history.

(56) References Cited

U.S. PATENT DOCUMENTS

| | | | | |
|---|---|---|---|---|
| 2001/0044136 A1* | 11/2001 | Lander | ............... | C12N 15/1003 435/91.1 |
| 2004/0038393 A1* | 2/2004 | Duarte | .................. | C12N 15/87 435/320.1 |

FOREIGN PATENT DOCUMENTS

| | | | | |
|---|---|---|---|---|
| WO | WO-9636706 A1 * | 11/1996 | ......... | C12N 15/1017 |
| WO | WO-2005026331 A2 * | 3/2005 | ......... | C12N 15/1003 |

* cited by examiner

*Primary Examiner* — Thane Underdahl
(74) *Attorney, Agent, or Firm* — Thomas S. Kim; Pathway Consulting Group

(57) ABSTRACT

Large scale processes for producing high purity samples of biologically active molecules of interest from bacterial cells are disclosed. The methods comprise the steps of producing a lysate solution by contacting a cell suspension of said plurality of cells with lysis solution; neutralizing said lysate solution with a neutralizing solution to produce a dispersion that comprises neutralized lysate solution and debris; filtering the dispersion through at least one filter; performing ion exchange separation on said neutralized lysate solution to produce an ion exchange eluate; and performing hydrophobic interaction separation on said ion exchange eluate to produce a hydrophobic interaction solution. Further, provided are compositions comprising large scale amounts of plasmid DNA produced by the disclosed large scale processes.

16 Claims, 3 Drawing Sheets

Figure 1

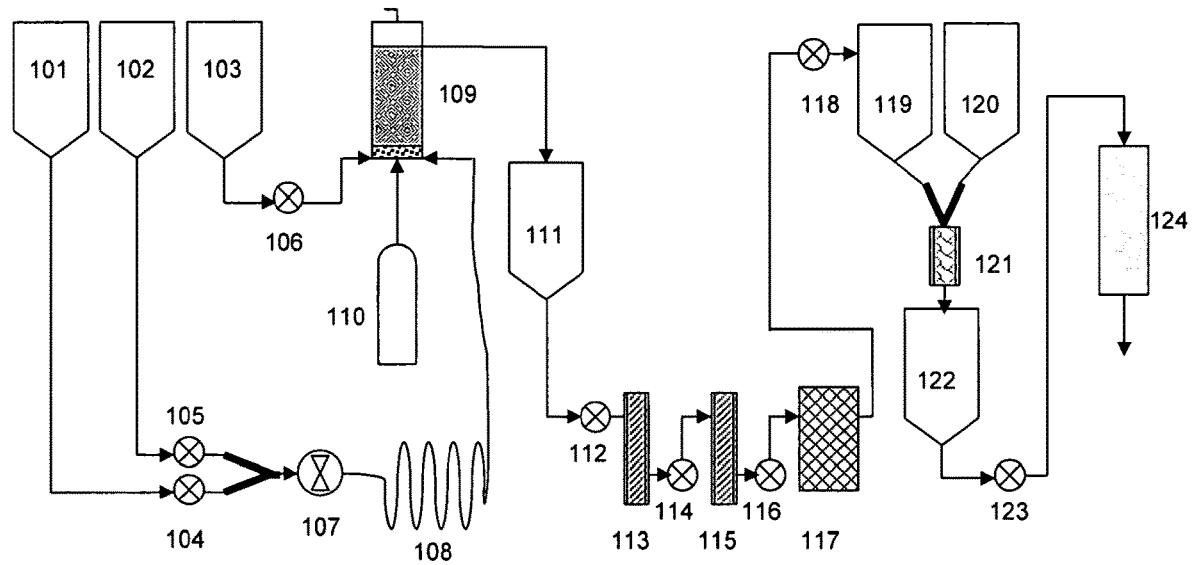

101: Cell resuspension tank
102: Lysis solution tank
103: NP solution tank
104: Pump for cell resuspension
105: Pump for lysis solution
106: Pump for NP solution
107: In-line mixer
108: Holding coil
109: Bubble column mixer
110: Compressed gas tank
111: Container for crude lysate
112: Pump for primary filtration
113: Primary filter
114: Pump for secondary filtration
115: Secondary filter
116: Pump for third filter (optional)
117: Third filter (optional)
118: Pump for clarified lysate
119: Container for clarified lysate
120: Water tank
121: Mixer
122: Container for diluted lysate
123: Pump for Mustang Q
124: Mustang Q cartridge Lane1: Supercoiled DNA ladder (Invitrogen)
Lane 2: Cell lysate containing plasmid A
Lane 3: Q eluate containing plasmid A
Lane 4: HIC eluate containing plasmid A
Lane 5: UF product of plasmid A Lane1: Supercoiled DNA ladder (Invitrogen)
Lane 2: Lysate from primary filtration
Lane 3: Lysate from secondary filtration
Lane 4: Lysate from third filtration
Lane 5: Eluate #1 from Mustang Q
Lane 6: Eluate #2 from Mustang Q

COMPOSITIONS COMPRISING HIGH CONCENTRATION OF BIOLOGICALLY ACTIVE MOLECULES AND PROCESSES FOR PREPARING THE SAME

CROSS REFERENCE TO RELATED APPLICATION

This application is a divisional of U.S. patent application Ser. No. 12/126,611, filed May 23, 2008, which claims the benefit of U.S. Provisional Application No. 60/939,792, filed May 23, 2007, the contents of which are each incorporated herein by reference.

FIELD OF THE INVENTION

The present invention relates to bulk compositions comprising biologically active molecules such as plasmids in high concentrations and processes for producing such compositions.

BACKGROUND OF THE INVENTION

There are numerous uses of biologically active molecules produced in and isolated from cells. U.S. Publication Serial No. 20050014245, which is incorporated herein by reference, discloses devices and methods for biomaterial production. Biologically active molecules include proteins and nucleic acid molecules. Production of such molecules in living cells offers numerous advantages over alternative productions methods but isolation and purification issues arise when extracting biologically active molecules from cells. There are various components present in cells which prevent realization of high yields of biologically active molecules of interest as well as representing possible unwanted contaminants to a final product.

Plasmid production is a field of interest due to the emergence of the non-viral gene therapy and DNA vaccine fields. Plasmids are large and complex macromolecules, which are maintained as supercoiled DNA structures unless disrupted. Rather then using synthetic means, in many instances it is more cost effective to produce them in biological systems, and subsequently isolate and purify them from those systems. Biological production of plasmids commonly takes the form of fermenting *Escherichia coli* ("*E. coli*") cells containing the plasmid of interest.

Cell lysis and the subsequent treatment steps used to prepare a process stream for purification, are the most difficult, complex, and important steps in any plasmid process. It is in this process where yield and quality are defined for each plasmid production run. The search for an optimal method, one which is continuous, scaleable, and yielding high quality product that can be formulated at high concentration irrespective of plasmid size, has been an obstacle in getting acceptable processes to commercial capability.

Lysing bacteria for plasmid purification using alkali and detergents is a common technique. Unfortunately, this method presents significant challenges for large scale preparations (or scaled-up production). First, thorough mixing of suspended cells with lysis solution is easily managed at small scale by simply vortexing or inverting the vessel containing the cells. However, this is impractical at large scale, where volumes may be in the range of tens or hundreds of liters. Common techniques for mixing large volumes of liquid, such as impeller mixing, are problematic because as some cells begin to lyse after initial mixing, they release genomic DNA which dramatically increases solution viscosity. This increase in viscosity significantly interferes with further mixing. Another challenge is that excessive incubation at high pH after addition of alkaline lysis solution can lead to permanent denaturation of the plasmid, making it unsuitable for most subsequent uses, especially for therapeutic purposes. Furthermore, it is well known that mixing at this step should be thorough but sufficiently gentle (i.e., low shear) to prevent substantial amounts of material from the flocculent precipitate into the plasmid-containing solution. Large amounts of host genomic DNA and endotoxin are present in the flocculent precipitate and if they become mixed with the plasmid they can be difficult to separate from the plasmid during subsequent purification. Thus, the large scale production of plasmids expose large quantities of cells to lysis solution, mix them and neutralize the lysate in a manner to optimize plasmid yield, minimize plasmid degradation, and maximize removal of other cellular components so that the material can be further purified to produce a high concentration, high quality, high purity final product in relatively large volumes.

There are a variety of existing methods to purify plasmids; however, these methods are not suitable for large scale preparations. Laboratory scale purification techniques cannot simply be scaled up for the volumes involved in large scale plasmid preparation. Large scale preparations require the optimization of yield and molecular integrity while maximizing removal of contaminants and concentration of plasmid. In producing large quantities of plasmid DNA at high concentration, a problem exists in maintaining the plasmid as supercoiled and open circle relaxed form. Storage conditions generally require high salt, and molecular degradation over time remains a problem even in the presence of salt. Many existing purification methods rely upon the use of potentially dangerous, toxic, mutagenic or contaminated substances, and/or expensive substances or equipment, which, again, are not desirable for large scale preparations. Some existing purification methods utilize the use of enzyme to digest protein for eventual elimination and such enzymes are costly for large scale production and can cause a risk of biologic contamination.

There remains a need for methods of large scale production of biologically active molecules of interest, such as plasmids, in which the final product can be produced in a cost effective manner, such as minimal equipment and/or minimal process steps, with high yield, at high concentration, and minimal degradation and without the presence of impurities, contaminants and unwanted substances. There remains a need for large quantities of plasmids solutions having high concentration and minimal degradation and presence of impurities, contaminants and unwanted substances and methods of preparing such solutions. The need for large quantities of plasmids is greater for those plasmids that are low copy number plasmids, which require much larger quantities of cells to yield plasmid quantities in the milligram ("mg") range and above.

SUMMARY OF THE INVENTION

An aspect of the present invention comprises large scale processes for producing high purity samples of at least one biologically active molecule of interest from bacterial cells. The large scale processes comprise the steps of:
  a) producing a lysate solution by contacting a cell suspension of said plurality of cells with lysis solution;
  b) neutralizing said lysate solution with a neutralizing solution to produce a dispersion that comprises neutralized lysate solution and debris;

c) filtering the dispersion through at least one filter;

d) performing ion exchange separation on said neutralized lysate solution to produce an ion exchange eluate; and e) performing hydrophobic interaction separation on said ion exchange eluate to produce a hydrophobic interaction solution. In some embodiments of this aspect, the large scale processes further includes the step of preparing a solution of at least one biologically active molecule by ultrafiltration of said hydrophobic interaction solution.

A further aspect of the present invention comprises large scale processes for producing high purity samples of at least one biologically active molecule of interest from bacterial cells, comprising the steps of: contacting the bacterial cells in a dispersion of cells with lysis solution to form a lysate solution; neutralizing the lysate solution by mixing a neutralization solution into the lysate solution with a bubble column mixer to form a neutralized mixture; filtering the neutralized mixture through a primary filter and a secondary filter to form a filtered solution; passing the filtered solution through an ion-exchange column to form a ion-exchange solution; passing the ion-exchange solution through a hydrophobic interaction column or a hydrophobic interaction membrane to form a hydrophobic interaction solution; and ultrafiltration of the hydrophobic interaction solution to form a high purity sample of at least one biologically active molecule of interest; wherein each transition from one step to a subsequent step in the large scale process from the contacting step to the passing the filtered solution step occur substantially continuously.

In another aspect of the present invention, provided are compositions comprising at least one biologically active molecule of interest prepared by the method described and disclosed herein, wherein at least one biologically active molecule of interest is a DNA plasmid. In some embodiments the compositions comprise at least one DNA plasmid at a quantity of about 10 mg or more in solution, wherein the high purity of said plasmids is the plasmids being present at greater than about 90%, 91%, 92%, 93%, 94%, 95%, 96%, 97%, 98%, or 99%.

BRIEF DESCRIPTION OF THE DRAWINGS

The numerous objects and advantages of the present invention may be better understood by those skilled in the art by reference to the accompanying figures, in which:

FIG. 1 displays a schematic of one embodiment that is used to isolate and purify biologically active molecules of interest from bacterial cells in a continuous flow process.

DESCRIPTION OF PREFERRED EMBODIMENTS

Figure 2:
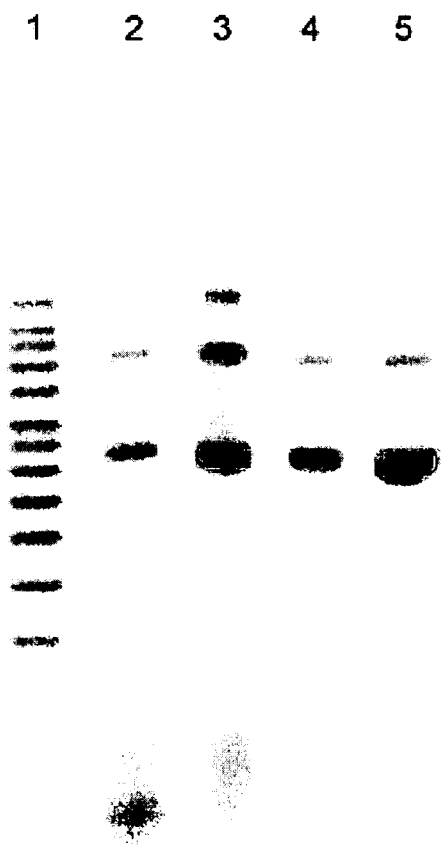
FIG. 2 displays a picture of an electrophoretic gel that includes samples from EXAMPLE 1, below. Lane 1 represents the supercoiled plasmid ladder (Invitrogen); Lane 2 the cell lysate; Lane 3 product after Q anion exchange; Lane 4 the product after purification with hydrophobic interaction; and lane 5 the final product blended after UF.

Methods of purifying biologically active molecules of interest from cells are provided so as to purify biologically active molecules of interest at high levels of purity and concentrations from the cells. Preferably the biologically active molecules of interest are plasmids or DNA plasmids. The cells may be any cells containing biologically active molecules of interest. In some embodiments, the cells are microbial cells such as for example prokaryotic cells such as bacterial cells. In some embodiments, they are *E. coli* cells. The cells may be produced or generated by any means, such as for example by fermentation. Methods for fermenting cells are well known to those skilled in the art. The present invention may be employed to extract any biologically active molecules of interest from cells. In some embodiments, the present invention may be employed to extract more than one type of biologically active molecule of interest. The biologically active molecules of interest may be a macromolecule such as a nucleic acid molecule or protein. In some embodiments, the biologically active molecule of interest may be a plasmid.

The term "plasmid" or "DNA plasmid," used interchangeably, refers to circular DNA molecules that are extrachromosomal DNA molecules separate from the chromosomal DNA which are capable of replicating independently of the chromosomal DNA. An encoding sequence or transgene is often contained within the DNA plasmid, and when present, the DNA plasmid is referred to as an expression plasmid or expression construct. The coding sequence, or "encoding nucleic acid sequence," can include initiation and termination signals operably linked to regulatory elements including a promoter and polyadenylation signal capable of directing expression in the cells of the individual to whom the nucleic acid molecule is administered.

The term "large scale" as used in reference to the described processes refers to purification processes that produce from bacterial cells or a suspension of bacterial cells quantities of at least one biologically active molecules, particularly DNA plasmid, of about 1 gram or greater and/or purification processes that requires lysis of quantities of bacterial cell paste of about 1 kilogram or greater.

The term "high purity" as used in reference to the level of purity of biologically active molecules, particularly DNA plasmid, refers to purification of the molecules from host bacterial cells at a level of at least greater than or equal to about 90%; and preferably greater than or equal to about 91%, greater than or equal to about 92%, greater than or equal to about 93%, greater than or equal to about 94%, greater than or equal to about 95%, greater than or equal to about 96%, greater than or equal to about 97%, greater than or equal to about 98%, or greater than or equal to about 99%.

The term "continuous" or "substantially continuous" as used in reference to the processes described herein refers to a continuous flow of materials (or solution or dispersion) between each step of the purification process to each subsequent step, starting from the beginning of the purification process up until the step of loading the ion-exchange chromatography column. For example, as bacterial cells of a dispersion contact with lysis solution in the contacting step to form a lysate solution, such lysate solution will directly flow into the next step of neutralization with the neutralization solution. These continuous transitions between steps eliminate a holding or incubating step between the purification process steps.

The term "biologically active molecule" refers to a molecule or a biomolecule contained within the bacteria that is in its functional state, and, in some embodiments, particularly refers to a DNA plasmid. Such DNA plasmids can be isolated and used to transfect cells of interest. The compositions of the present invention comprise at least one type of biological active molecule. In some embodiments, the compositions of the present invention comprise more than one type of biological active molecules.

Plasmids vary widely in their copy number depending on the origin of replication they contain, e.g., pMB1 or pSC101, which determines whether they are under relaxed or stringent control; as well as the size of the plasmid and its associated inserted sequences. Some plasmids, such as the pUC series and derivatives, have mutations which allow them to reach very high copy numbers within the bacterial cell. Plasmids based on pBR322 are generally maintained at lower copy numbers. Very large plasmids are often maintained at very low copy numbers per cell. Some embodiments of the present invention relate to a plasmid purification process that allows for purifying plasmids from cells, preferably bacterial cells, in large scale to yield large quantities of plasmid, such as gram quantities, in cost-efficient and minimal-steps manufacturing process (in order to maintain higher yields). In some embodiments, the plasmid is a low copy number plasmid. For purposes of the process provided and the resulting biologically active molecules produced, a low copy number plasmid is a plasmid that achieves a copy number of less than or equal to about 300, less than or equal to about 100, less than or equal to about 50, less than or equal to about 20, less than or equal to about 10, or less than or equal to about 5.

An aspect of the present invention comprises large scale processes for producing high purity samples of at least one biologically active molecule of interest from bacterial cells. The processes comprise the steps of:

a) producing a lysate solution by contacting a cell suspension of said plurality of cells with lysis solution;

b) neutralizing said lysate solution with a neutralizing solution to produce a dispersion that comprises neutralized lysate solution and debris;

c) filtering the dispersion through at least one filter;

d) performing ion exchange separation on said neutralized lysate solution to produce an ion exchange eluate; and e) performing hydrophobic interaction separation on said ion exchange eluate to produce a hydrophobic interaction solution.

In an embodiment, the large scale processes comprise a producing lysate solution step that comprises mixing said cell suspension with lysis solution in a high shear, in-line mixer.

In some embodiments, the producing step comprises contacting the cell suspension with the lysis solution in a mixer over a duration of from about 1 minutes to about 20 minutes, preferably from about 4 minutes to about 8 minutes, and more preferably for about 5 minutes. In some embodiments, the neutralizing step comprises mixing the lysate solution with the neutralizing solution in a bubble mixer. In some embodiments, the performing hydrophobic interaction separation step comprises performing hydrophobic interaction separation using a hydrophobic interaction column or a hydrophobic interaction membrane to form a hydrophobic interaction solution. The hydrophobic interaction separation step can be separation of the biologically active molecule of interest by binding to a hydrophobic interaction membrane or column, which enables impurities to flow through or be washed off. In some embodiments, the biologically active molecule of interest may flow through a hydrophobic interaction column while impurities bind. In some embodiments, the biologically active molecules of interest flow through a hydrophobic interaction membrane (or HIC membrane) (referred to herein as "Method I"). In some embodiments, the biologically active molecules of interest bind to a HIC column, such as a butyl column (referred to herein as "Method II"). In some embodiments, a combination of HIC membrane and HIC column, such as a butyl column, may be used (referred to herein as "Method III") to yield large-scale amounts of biologically active molecule of interest with high purity, such as gram or greater quantities of DNA plasmids. In some embodiments, the hydrophobic interaction separation comprises separation using at least butyl hydrophobic interaction chromatography in order to produce a hydrophobic interaction solution that is a butyl hydrophobic interaction chromatography solution eluate.

In some embodiments, the described large scale processes can further include a step of preparing a solution of at least one biologically active molecule by ultrafiltration of said hydrophobic interaction solution. Furthermore, a step of preparing a sterile solution of biologically active molecules by sterile filtration of said solution of biologically active molecules can be performed.

In some embodiments, the large scale processes include a holding step that requires holding the dispersion for a period of time to separate the neutralized lysate solution from the debris, and then filtering the neutralized lysate solution through at least one filter.

In some embodiments, the performing ion exchange separation step is performed using an anion exchange membrane. Preferably, the ion exchange separation step comprises use of an ion exchange column, and preferably using a Mustang® Q cartridge.

In some embodiments, the large scale processes include continuous processes or is referred to as a continuous large scale process for production of high purity biologically active molecules from bacterial cells. The method comprises transitioning from one step to a subsequent step of the large scale process substantially continuously and comprises separating the neutralized lysate solution from the debris in the dispersion by collecting the lysate in a container and passing the dispersion through a primary filter to produce an initial crude neutralized lysate solution. In some embodiments, the processes further comprises passing the first crude neutralized lysate solution through a secondary filter to produce a subsequent crude neutralized lysate solution.

In an embodiment, the present invention comprises large scale processes for producing high purity samples of biologically active molecules of interest from bacterial cells, comprising the steps of: contacting the bacterial cells in a dispersion of cells with lysis solution to form a lysate solution; neutralizing the lysate solution by mixing a neutralization solution into the lysate solution with a bubble column mixer to form a neutralized mixture; filtering the neutralized mixture through a primary filter and a secondary filter to form a filtered solution; passing the filtered solution through an ion-exchange column to form a ion-exchange solution; passing the ion-exchange solution through a hydrophobic interaction column or a hydrophobic interaction membrane to form a hydrophobic interaction solution; and ultrafiltration of the hydrophobic interaction solution to form a high purity sample of biologically active molecules of interest; wherein each transition from one step to a subsequent step in the large scale process from the contacting step to the passing the filtered solution step occur substantially continuously. In another aspect of the present invention, provided are compositions comprising biologically active molecules of interest prepared by the described large scale processes herein, wherein the biologically active molecules of interest are DNA plasmids. In some embodiments the compositions comprise DNA plasmids at a quantity of about 10 mg or more in solution, wherein the high purity of said plasmids is the plasmids being present at greater than about 90%, 91%, 92%, 93%, 94%, 95%, 96%, 97%, 98%, or 99%. The composition of claim 18, wherein said concentration of plasmid is about 5, 6, 7, 8, 9, 10, 11, 12, or 13 mg/mL. Some compositions include plasmid at a level of greater than about 50%, 55%, 60%, 65%, 70%, 75%, 80%, 81%, 82%, 83%, 84%, 85%, 86%, 87%, 88%, 89%, 90%, 91%, 92%, 93%, 94% or 95% supercoiled plasmid, and preferably greater 80% supercoiled plasmid. Some compositions contain less than or equal to about 10 EU endotoxin per mg of plasmid, and some embodiments, the compositions, less than or equal to about 1 EU endotoxin per mg of plasmid. Some embodiments less than or equal to about 0.1 EU endotoxin per mg of plasmid. In some embodiments, the compositions include solution containing less than or equal to about 1.0% RNA or less than or equal to about 0.4% RNA. In some preferred embodiments, the compositions include solution containing less than or equal to about 1.0% protein, preferably less than or equal to about 0.20% protein. In some embodiments, the compositions include solution containing less than or equal to about 1% genomic DNA, preferably less than or equal to about 0.01% genomic DNA.

An example of an embodiment of the present invention which includes many of the process steps provided herein, includes the following steps: first step, cells of interest are produced and harvested; second step, cells are lysed to release their contents, including the biologically active molecules of interest, into solution; third step, solid cell debris and precipitated cell components are separated from the fluid containing at least one biologically active molecule of interest; fourth step, solutions containing the biologically active molecules of interest are subjected to ion exchange chromatography; fifth step, the partially purified material resulting from ion exchange chromatography is subjected to hydrophobic interaction chromatography; sixth step, the material resulting from hydrophobic interaction chromatography is subjected to ultrafiltration and diafiltration, to concentrate at least one type of biologically active molecules of interest, and to remove excess salts from the solution; seventh step, the concentrated and desalted product is optionally subjected to sterile filtration, to render it suitable for pharmaceutical uses, including, for example, intramuscular delivery, intravenous delivery, intranasal delivery, intracardiac delivery, aerosol delivery, transdermal delivery, in vivo electroporation facilitated delivery to muscle, in vivo electroporation facilitated delivery to subcutaneous or intradermal tissue, as well as other known methods of pharmaceutical administration.

Some embodiments of the invention include the process steps disclosed herein, including, but not limited to the operation of a combination of steps in a continuous mode resulting in the scale of production which is not limited by the process hold steps. Such processes enable the production of pharmaceutical grade biomolecules at large scale, e.g. production of about 1 gram or more of plasmid. Some embodiments of the invention exclude the use of any materials or processes that could prove detrimental to the large scale production or pharmaceutical products include, for example, the inclusion of enzymes, heat denaturation, mechanical separation (machines that do such separation), e.g., centrifugation apparatus, or organic or volatile solvents, e.g., isopropanol.

Cells of interest may be produced and harvested such as by routine means of fermentation and collection. It is well within the abilities of one skilled in the art to prepare sufficient quantities of the cells of interest. For example, the cells may be *E. coli* containing a high copy number plasmid of interest, and the plasmid-containing cells may be fermented to high density using batch or fed batch techniques. Methods for preparing such plasmid-containing *E. coli* cells and performing such batch or fed-batch fermentation are well known to those skilled in the art. The cells may be harvested by routine means such as centrifugation or filtration to form a cell óaste. Such harvesting methods are well known to those skilled in the art. Furthermore, those skilled in the art will recognize that harvested cells or cell paste may be processed immediately, or stored in a frozen or refrigerated state for processing at a later date.

Harvested cells may be lysed using a lysis solution to release their contents, including the biologically active molecules of interest, into a lysate solution.

Generally, prior to lysing the cells, the cell paste may be used to prepare a suspension of cells containing the biologically active molecule of interest. The cells may be suspended in any suitable solution. The suspension containing the cells in suspension solution may be maintained in a tank or other storage container. Two containers may be used wherein the second container may be used to resuspend additional amount of cells while the first container is used in the lysis process. The suspension solution may in some embodiments contain a moderate concentration of buffer, a moderate concentration of a chelating agent, or both. In some embodiments, the suspension solution may comprise about 25 mM Tris-hydrochloride ("Tris-HCl"), and about 10 mM edetate disodium ("Na$_2$EDTA"), at a pH of about 8. In some embodiments, the cell suspension may be prepared by suspending a known weight of cell paste with a known weight of suspension buffer. For example, one part cell paste may be resuspended in about 4-10 parts of buffer, in some embodiments with about 6-8 parts of buffer. In some embodiments, the optical density of the resulting cell suspension may be about 50-80 OD$_{600}$ units. In some embodiments, it may be about 60-70 OD$_{600}$ units.

A lysis solution preferably contains one or more lysis agents, such as an alkali, an acid, an enzyme, an organic solvent, a detergent, or a mixture thereof. However, the use of an animal derived enzymes or organic solvent is not preferred as they are detrimental to the production of pharmaceutical products. In some embodiments, the lysis solution comprises an alkali, a detergent, or a mixture thereof. Suitable alkalis include, but are not limited to, sodium hydroxide or potassium hydroxide. Detergents may be non-ionic, cationic, or anionic. Suitable detergents include, but are not limited to sodium dodecyl sulfate ("SDS"), Triton, Tween, or pluronic-type agents (block-copolymers based on ethylenoxide and propylenoxide). Selection of suitable alkali or detergent will be well within the ordinary skill of the art. In some embodiments, the lysis solution may comprise sodium hydroxide ("NaOH") and SDS. In some embodiments, the concentration of NaOH may be about 0.1 to about 0.3 N, and in some embodiments, about 0.2 N. In some embodiments, the concentration of SDS may be about 0.1% to about 5%, and in some embodiments about 1%. In some embodiments, the lysis solution may be maintained in a tank or other storage container.

The cell suspension and lysis solution may be combined to lyse the cells and produce a lysate solution. In some embodiments, they are combined, mixed and maintained as a mixture for a time sufficient to facilitate high levels of lysis of cells and release of biological materials, thus forming the lysate solution.

In some embodiments, cell suspension and lysis solution are maintained in separate tanks and retrieved from such tanks using one or more pumps. The cell suspension and lysis solution may be brought into contact with each other using a "Y" connector. In some embodiments, equal volumes of cell suspension and lysis solution may be pumped at equal flow rates using a dual head pump. However, those of skill in the art will recognize that cell suspension and lysis solution of different volumes may be pumped at different rates, using individual pumps, if so desired. In some embodiment, cell suspension and lysis solution are simultaneously pumped through a dual head pump frp, from about 0.3 L/min to about 2 L/min, with the contacted fluids exiting the "Y" connector at a rate from about 0.6 L/min to about 4 L/min. Those of skill in the art will recognize that these flow rates can be easily increased or decreased, and tubing size increased or decreased, to meet any throughput requirement. After exiting the "Y" connector, the contacted cell suspension and lysis solution may be passed through a high shear, in-line mixer. The mixer may be any device that provides rapid, high shear mixing in a flow through mode (as opposed to a batch mode). In some embodiments, the mixer is a rotor/stator mixer or an emulsifier. Those of skill in the art will recognize that a variety such high shear, in-line mixers are commercially available. Use of any such mixers is well within the scope of the present invention. In some embodiments, the mixer is a Silverson L4R rotor/stator mixer fitted with a standard Emulsor screen (Silverson Machines, Inc. East Longmeadow, Mass.) and an in-line assembly. The rotor may be operated at a speed such as from about 500 rpm to about 900 rpm, 500-600 rpm, from about 500 rpm to about 700 rpm, from about 500 rpm to about 800 rpm, from about 600 rpm to about 700 rpm, from about 600 rpm to about 800 rpm, from about 600 rpm to about 900 rpm, from about 700 rpm to about 800 rpm or from about 700 rpm to about 900 rpm. Such a mixer is suitable for processing cell suspensions of from about 0.3 L/min to about 2 L/min. However, one skilled in the art will recognize that larger scale mixers may be substituted for processing substantially greater volumes of cell suspension. Such substitution will be readily accomplished by one skilled in the art with no more than ordinary experimentation. The use of a high shear, in-line mixer facilitates the thorough and rapid mixing of the cell suspension and lysis solution, bringing the cells into intimate contact with the lysis agent(s) to achieve efficient lysis. Moreover, mixers can readily accommodate different fluid flow rates, and provide the flexibility of adjustable speed mixing for different flow rates. Materials exiting the high shear, in-line mixer may then pass through a holding coil. This coil may simply comprise a length of tubing sufficient to provide that the fluid passes through the coil for a determined time. The function of the coil is to provide sufficient contact time between the cells and the lysis agent(s) to ensure substantially complete lysis. At the same time, the coil ensures that contact time is not so long as to have negative consequences. In some embodiments, such as those in which the cells are plasmid-containing cells and the lysis solution comprises an alkali, it is desirable to ensure that exposure to alkali lasts long enough to achieve substantially complete cell lysis as well as substantially complete denaturation of proteins, genomic DNA, and other cell components. However, it is also desirable that exposure to alkali not be so prolonged as to result in substantial amounts of permanently denatured plasmid. The coil may be one complete tubing, or segmented into 2-10 tubings to allow for flexibility of fluid flow rates. The holding coil allows this contact time to be controlled. In some embodiments this contact time may be from about 2 minutes to about 10 minutes. In some embodiments this contact time may be from about 2 minutes to about 9 minutes, from about 2 minutes to about 8 minutes, from about 2 minutes to about 7 minutes, from about 2 minutes to about 6 minutes, from about 3 minutes to about 10 minutes, from about 3 minutes to about 9 minutes, from about 3 minutes to about 8 minutes, from about 3 minutes to about 7 minutes, from about 3 minutes to about 6 minutes, from about 4 minutes to about 10 minutes, from about 4 minutes to about 9 minutes, from about 4 minutes to about 8 minutes, from about 4 minutes to about 7 minutes, from about 4 minutes to about 6 minutes, from about 5 minutes to about 10 minutes, from about 5 minutes to about 9 minutes, from about 5 minutes to about 8 minutes, from about 5 minutes to about 7 minutes, or from about 5 minutes to about 6 minutes. Preferably the contact time is from about 4 minutes to about 8 minutes or from about 4 minutes to about 6 minutes. In some embodiments the contact time is about 5 minutes. In some embodiments, the length and diameter of the holding coil are such that the desired exposure time is achieved when lysed cells are flowed through at the desired rate. In some embodiments, the holding coil may be from about 10 feet in length to about 150 feet in length, from about 25 feet in length to about 100 feet in length, or from about 40 feet in length to about 60 feet in length. In some embodiments the holding coil is about 50 feet in length, and in some embodiments the holding coil is about 100 feet in length. The holding coil can have an inner diameter from about 0.5 inches to about 2 inches, and in some embodiments 0.625 inches. Also in some embodiments, the lysed cells may exit the high shear, in-line mixer and pass through the holding coil at a rate of from about 100 mL/min to about 10 L/min, from about 200 mL/min to about 8 L/min, from about 300 mL/min to about 6 L/min, from about 400 mL/min to about 4 L/min, from about 400 mL/min to about 2 L/min, or from about 600 mL/min to about 1.2 L/min. Preferably the rate through the holding coil is from about 0.6 L/min to about 10 L/min. In some preferred embodiments the rate of passage through the holding coil is about 600 mL/min and in some embodiments it is about 1200 mL/min. Adjustment of coil length and diameter can be accomplished by one skilled in the art to accommodate or adjust to the larger flow rate as biologically active molecule production is scaled-up. The lysate solution is collected from the holding coil.

The lysate solution is neutralized by combining it with a neutralizing solution (which is also referred to as a neutralizing precipitation solution) to produce a dispersion comprising neutralized lysate solution and debris. The resultant dispersion may then be maintained to facilitate separation of the neutralized lysate solution from the debris.

In some embodiments, lysate solution, which comprises the lysed cells, may be neutralized by mixing it with neutralizing solution in a neutralizing chamber. This neutralization of lysate solution can be facilitated by mixing in the neutralizing chamber. In some embodiments, this neutralizing can be followed by bubble mixing in a bubble column mixer. Preferably, the neutralization occurs in conjunction with bubble mixing in a bubble column mixer. In some embodiments, the lysate solution exiting the holding coil may enter a bubble column mixer while simultaneously a pump may deliver a neutralization/precipitation solution from another tank into the bubble column mixer. In some examples, also simultaneously, compressed gas from another tank may be sparged into the bottom of the bubble column mixer. In some embodiments, lysate solution may enter the column at the bottom from one side, while neutralization/precipitation solution may enter at the bottom from the opposite side. Compressed gas may be sparged in through a sintered sparger designed to deliver gas bubbles substantially uniformly across the column cross section. Lysate solution, which comprises the lysed cells, and neutralization solution flow vertically up the column and exit through an outlet port on the side near the top. The passage of the gas bubbles through the vertical column of liquid serves to mix the lysate solution with the neutralization/precipitation solution. The mixing provided by the rising gas bubbles is thorough but gentle and low shear. As the neutralization/precipitation solution mixes with the lysed cells of the lysate solution, cell components precipitate from the solution. A snorkel may be provided at the top of the bubble column mixer to vent excess gas.

In some embodiments, the lysate solution comprises plasmid-containing cells lysed with an alkali, a detergent, or a mixture thereof, and the neutralizing/precipitating solution neutralizes the alkali and precipitates host cell components such as proteins, membranes, endotoxins, and genomic DNA. In some embodiments, the alkali may be NaOH, the detergent may be SDS, and the neutralization/precipitation solution may comprise potassium acetate, ammonium acetate, or a mixture thereof. In some embodiments, the neutralization/precipitation solution may comprise an unbuffered solution containing about 1 M potassium acetate and from about 3 M to about 7 M ammonium acetate. Using such a neutralization/precipitation solution produces a suspension with a pH of from about 7 to about 8, which is preferable to an acidic pH because acidic conditions can lead to depurination of DNA. In some embodiments, the neutralization/precipitation solution may be provided in a chilled form from about 2° C. to about 8° C.

The bubble column mixer provides mixing in a low shear manner and thus avoids excessive release of genomic DNA and endotoxins into the neutralized lysate solution. One skilled in the art will be able to determine suitable rates for flowing gas through the bubble column mixer. Gas flow rates may be used at about 2 standard liters per minute to about 20 standard liters per minute ("slpm"). Any suitable gas may be used, including, but not limited to, air, nitrogen, argon, and carbon dioxide. The gas may be filtered compressed air.

The combination of lysate solution and neutralization solution results in the generation of a dispersion containing neutralized lysate solution and debris. The neutralized lysate solution may be collected in a tank or other storage container. In some embodiments, the container is chilled to 5-10° C. The time for the holding of neutralized lysate in the container is not mandatory, and may vary from less than 1 hour, from about 1 hour to about 12 hours, from about 12 hours to about 15 hours, or greater than 15 hours. In some embodiments, the time used is about 12 hours, while some examples involve a time of about 15 hours, while in other examples the time is "overnight" (defined as being greater than about 15 hours). In one embodiment, a sufficient hold period was employed to achieve substantially complete separation of the cell debris from the neutralized lysate solution, resulting the obtained crude lysate of limited solid particles advantageous for subsequent clarification process. However, the process scale is limited to the crude lysate holding tank and the process time is elongated by this hold period.

In order to achieve large scale purification of low yield plasmid product, the period for the holding of neutralized lysate may be reduced to lower than 1 hour. In some embodiments, the neutralized lysate solution may be simultaneously processed at the time it is generated, thus the holding time in the container is negligible. In some embodiments, the lysate solution is simultaneously processed by the following process after a period from about 5 minutes to about 60 minutes of collecting the lysate in the container. The reduction or elimination of lysate holding time also removes the process capacity limit by containers as the lysate is processed immediately at its generation.

The neutralized lysate solution may be clarified with any approaches of solid/liquid separation, e.g. bag filtration, cartridge filtration, batch centrifugation, continuous centrifugation. Complete removal of the particles in the solution is desirable to avoid the clogging of membrane or column in the following purification processes. At the same time, the lysate may not be subjected to excessive shear that will shred genomic DNA and cause the release of genomic DNA, shredded genomic DNA, endotoxin and other contaminants to be released into the plasmid-containing solution. Batch filtration may be used for processing small volume of lysate, but impractical at large scale. Continuous centrifugation is also unsuitable because the precipitate may be subjected to high shear stress and release high level of contaminant to solution. In some embodiments a series of filtrations employing different grade of filter media can be utilized. The primary filtration can be used to remove a majority of large cell floccs range in micron sizes, while the consecutive secondary filtration retains the remaining fine particles. An optional third filtration may be conducted when a stringent clarity is desired for the following process and the secondary filtration is insufficient.

In some embodiments, bag and cartridge filters can be employed due to their high dirt holding capacity and minimal disturbance to solution. The filter bags or cartridge may be of any size, shape, pore size rating, configuration, and media type. The filter media is preferred to be made of materials of pharmaceutical grade or compliant with Food and Drug Administration (FDA) requirements. The filter material is also preferred to have no charge or have limited binding of the product. The particle size limit of filter materials may vary from about 0.1 µm to about a few hundred microns, providing that it is greater than the size of the target product that the product will not be retained by the filter media. The bag filters and cartridge filter media may be single-layered, multi-layered, pleated, or multi-pleated.

In some embodiments, two or more filters with similar pore size ratings may be used in parallel to accommodate process at large scale. The majority of solid particles in the lysate solution, including cell wall and membrane components, precipitates, genomic DNA, protein, lipids, lipopolysaccharides, and other contaminants, will be removed by the filtration. However, when the primary filtration is insufficient to deliver solution of desired clarity, a secondary filtration with reduced pore size or higher retention rate may be placed subsequently. In some embodiments, two or more secondary filters may be placed in parallel to accommodate process at large scale. Use of multiple filters may be required in a large scale process, and one skilled in the art will recognize that details such as the number of filters used, as well as their particle size limits, may be readily varied.

In some embodiments, the dispersion may be collected and maintained in a settling tank to allow the debris to precipitate or float. Accordingly, in some embodiments, the dispersion may be collected as a slurry of crude cell lysate and precipitated host cell components from the bubble column mixer and maintained in a settling tank to allow the debris to precipitate or float. The dispersion may be maintained, such as being held in the settling tank, for a time sufficient to achieve substantially complete separation of the precipitated host cell components, which make up the debris, from the neutralized lysate solution. The precipitated components may rise to the surface of the dispersion, aided by the entrapped gas bubbles introduced by the bubble column mixer. In some embodiments, the dispersion may be held in the settling tank for about 6 to about 24 hours, in some embodiments from about 12 hours to about 18 hours. In some embodiments, the dispersion may be chilled to less than about 15° C. during the holding period, in some embodiments from about 2° C. to about 8° C., to aid in precipitating RNA or other impurities. In some embodiments, the dispersion may be gently mixed during the holding period, such as by an impeller mixer operated at a very low rpm, preferably from about 15 rpm to about 25 rpm.

In some embodiments, a vacuum may be applied to the container which holds the dispersion, such as, for example, a settling tank. This aids in bringing precipitated components to the liquid surface. Furthermore, this compacts the floating flocculent precipitate/debris, aiding its subsequent removal and also allowing a greater percentage of neutralized lysate solution to be recovered in later steps. Furthermore, this removes air trapped in solution that may foul later chromatography steps. In some embodiments, the applied vacuum may be from about 15 inches of HG to about 30 inches of Hg (in·Hg), in some embodiments, from about 20 in Hg to about 30 in·Hg, and in some embodiments, from about 25 in Hg to about 30 in·Hg. In some embodiments, the vacuum may be maintained throughout this holding period. Vacuum may be applied using a vacuum pump, or any other available vacuum or negative pressure device available. In some embodiments, prior to beginning solid/liquid separation, any vacuum applied to the tank is carefully released. Crude cell lysate, i.e., neutralized lysate solution, is then collected from the tank using a pump and passed through a depth filter and a final filter, and then collected in a holding tank. In some embodiments, the settling tank is fitted with a sight glass, allowing an operator to observe the position of the liquid level and the compacted precipitated host cell components. Pumping of material from the tank is monitored visually, and halted before the precipitated host cell components enter the line. This prevents clogging of the subsequent filters. No bag filtration (or cartridge filtration) or centrifugation is required. Further, disturbance of the debris is thus minimizing release of components such as genomic DNA or endotoxins into the neutralized lysate solution. After the neutralized lysate solution is pumped from the settling tank, it may be passed through one or more filters to remove fine particulates. In some embodiments, about one to about three filters may be used in series, with the first filter removing larger particles, and subsequent filters removing successively smaller particles. In some embodiments, two filters may be used in series. In some embodiments, the first filter is a pre-filtering depth filter with a particle size limit from about 5 µm to about 15 µm, preferably from about 7.5 µm to about 12 or more preferably from about 9 µm to about 11 In some embodiments the pre-filtering depth filter has a particle size limit of about 10 The second filter is preferably a membrane filter with a cut-off of from about 0.01 µm to about 0.25 or preferably from about 0.05 µm to about 0.15 µm. In some embodiments the membrane filter has a cut-off of about 0.1 µm. However, one skilled in the art will recognize that details such as the number of filters used, as well as their particle size limits, may be readily varied.

A large selection of filters is commercially available from different vendors. One particular type is 720 series pleated cartridge filters (CPI filters, Houston, Tex.), which demonstrated a large dirt holding ability and superior processing capacity. High efficiency multi-layer filter bags such as 300 series and 500 series (Knight Corporation, Houston, Tex.) have showed considerable retention to fine particles. PROGAF™ filter bags (Eaton Filtration, Cleveland, Ohio) with progressive density design of up to 12 layers of media may deliver high efficiency in the removal of particles with a variety of sizes. In some embodiments, a combination of pleated cartridge filtration followed by multilayer or pleated cartridge filtration may deliver best performance for the clarification of particles in the neutralized lysate solution.

The cartridge filters or bag filters are preferred to be assembled in the filter housings or filter vessels for the ease of operation and higher process capacity. The vessel material may be type 304 or 316 stainless steel, or carbon steel, while all plastic housing with a choice of polyvinyl chloride (PVC), chlorinated polyvinyl chloride (CPVC), polyester plastic (PPL) or polyvinylidene fluoride (PVDF) construction may be advantageous for ultra-pure or corrosive applications. The filter vessels may be custom-designed or readily available from several manufacturers. For example, Eaton Filtration (Cleveland, Ohio) provides a wide selection of housings/vessels designed to meet any demanding applications, such as TOPLINE, SIDELINE, DUOLINE, MODULINE, POLYLINE, FLOWLINE, ECOLINE, MAXILINE series. One skilled in the art will be able to determine the construct and features of filter housing to accommodate the process requirements.

Optionally, an additional depth filter or membrane filter may be implemented after the secondary filtration. The filter is preferred to have a cut-off of from about 0.1 µm to about 0.2 µm for further removal of fine particles in the neutralized lysate solution. Cartridge filters, such as Vangard PP and Alpha PP from Meissner (Camarillo, Calif.), Clarigard from Millipore (Billerica, Mass.), HP and PreFlow from Pall (East Hills, N.Y.), may be contemplated as disposable or with the aid of housings. However, most of these cartridge filters are limited by their process capacity, especially in the disposable formats. Preferable is the use of disposable components which may offer scalable format to accommodate applications at large scale. Millipore (Billerica, Mass.) has developed a high-performance disposable depth filter system, Millistak+ Pod, for the applications in either the lab or process-scale. The filter media in the pod filters is composed of select grade cellulose fiber and diatomaceous earth, and is demonstrated to have large contaminant holding and superior retention. The stacked disc design of pod format aid by the stainless holder enabled large surface area filtration in tight spaces. One skilled in the art may determine the media grade and membrane area of the Pod filter to meet specific operation needs.

The clarified neutralized lysate solution, which contains the biologically active molecules of interest, can then be subjected to ion exchange chromatography, including column chromatography or membrane based. Preferably, a membrane-based approach may be used, such as anion exchange membrane chromatography. For example, the neutralized lysate solution can be applied to an ion exchange membrane. According to some embodiments, the biologically active molecule of interest may contacted with a membrane whereby the biologically active molecule of interest may bind to the membrane, while impurities flow through or are washed off of the membrane, thus separating the biologically active molecule of interest from the impurities. Alternatively, the biologically active molecule of interest may flow through the membrane, while impurities are retained. In some embodiments, the biologically active molecule of interest binds to the membrane and, after washing to remove weakly bound impurities, the biologically active molecule of interest is eluted from the membrane. The elution may be accomplished by flowing a salt solution through the membrane. The salt solution has a strength, concentration, or conductivity sufficient to overcome the binding of the biologically active molecule of interest to the membrane. The biologically active molecule of interest is thus recovered in the ion exchange eluate.

Although any ion exchange membrane may be suitable, in some embodiments an anion exchange membrane such as a strong anion exchange membrane, comprising quaternary amine groups, may be used. Examples of such membranes include, but may not be limited to the Mustang Q (Pall Corporation, East Hills, N.Y.), Sartobind Q (Sartorius, Edgewood, N.Y.), and Intercept Q (Millipore Corporate, Billerica, Mass.).

In some embodiments, plasmid-containing cells are lysed and neutralized to produce a neutralized lysate solution that may be processed by anion exchange membrane purification that comprises purification using a Pall Mustang Q cartridge (Pall Corporation, East Hills, N.Y.). In some embodiments, the neutralized lysate solution may be adjusted to a conductivity of about less than 95 mS/cm, or about 85 mS/cm, by dilution with a suitable amount of purified water. The conductivity may be adjusted to from about 80 mS/cm to about 85 mS/cm in some embodiments. Purified water equal to about 1.5-times the lysate volume can be used for dilution to achieve the desired conductivity. The Mustang® Q cartridge may be conditioned by flowing a suitable salt solution through it. In some embodiments, the solution may comprise from about 0.5 M sodium chloride to about 1.0 M sodium chloride ("NaCl") and in some other embodiments 0.67 M NaCl. The equilibration solution may also include a buffering agent, a chelating agent, or a combination thereof. In some embodiments, this equilibration/wash solution may comprise, in addition to 0.67 M NaCl, 10 mM Tris-HCl, 1 mM $Na_2EDTA$, with a pH of 8. In some embodiments, equilibration/wash solution may be pumped through the cartridge at about 800 mL/min to about 1500 mL/min. Diluted neutralized lysate solution may be pumped onto the cartridge, in some embodiments at less than about 4800 mL/min, in some embodiments at from about 2000 mL/min to about 20,000 mL/min. The loaded cartridge may be washed with equilibration/wash buffer, preferably at a flow rate from about 800 mL/min to about 1500 mL/min. Washing may in some embodiments be continued until the absorbance at 260 nm ($A_{260}$) of the effluent returns to approximately baseline. Plasmid may be eluted with a solution that comprises 1 M NaCl, 10 mM Tris-HCl, 1 mM $Na_2EDTA$, and pH 8. Elution may in some embodiments be performed at a flow rate of from about 500 mL/min to about 9000 mL/min, from about 500 mL/min to about 8000 mL/min, from about 500 mL/min to about 7000 mL/min, from about 500 mL/min to about 6000 mL/min, from about 500 mL/min to about 5000 mL/min, from about 500 mL/min to about 4000 mL/min, from about 500 mL/min to about 3000 mL/min, from about 500 mL/min to about 2000 mL/min, from about 600 mL/min to about 5000 mL/min, from about 600 mL/min to about 4000 mL/min, from about 600 mL/min to about 3000 mL/min, from about 600 mL/min to about 2000 mL/min, or from about 600 mL/min to about 1500 mL/min. In some embodiments elution is continued until the $A_{260}$ of the eluate returns to about baseline. Those of skill in the art will recognize that flow rates can be easily increased by using large membrane areas and that the specific salts concentrations of the solutions listed can be altered to maximize the yield and purity of specific biomolecules using no more than ordinary experimentation. The eluate collected is ion exchange eluate and is used in subsequent purification by hydrophobic interaction steps.

The ion exchange eluate recovered from the ion exchange membrane is subjected to purification by hydrophobic interaction chromatography (herein, "HIC"). In some embodiments, the biologically active molecule of interest may bind to the HIC membrane or column, while impurities flow through or are washed off. In some embodiments, the biologically active molecule of interest may flow through while impurities bind. In some embodiments, the biologically active molecule of interest flow through a HIC membrane (referred to herein as "Method I"). In some embodiments, the biologically active molecules of interest bind to a HIC column, such as a butyl column (referred to herein as "Method II"). In some embodiments, a combination of HIC membrane and HIC column, such as a butyl column, may be used (referred to herein as "Method III") to yield large-scale amounts of biologically active molecule of interest with high purity.

The ion exchange eluate may be conditioned prior to flow onto the hydrophobic interaction membrane. Typically, the conditioning consists of adding a desired amount of a desired salt. In some embodiments, ammonium sulfate may be used in an amount suitable to provide binding of the product or the impurities, as desired. Typically, in methods III, no conditioning may be necessary for the HIC filtrate before loading to butyl column.

In some embodiments, ion exchange eluate is produced by anion exchange chromatography using a Pall Mustang® Q cartridge and further purified by hydrophobic interaction. In some embodiments, a HIC membrane such as a Pall Kleenpak™ Nova capsule (Pall Corporation, East Hills, N.Y.) with Supor PES filters may be used. The cartridge may be conditioned by flowing an equilibration/wash solution comprising concentration ammonium sulfate through it. In some embodiments, the equilibration/wash solution comprises from about 1 M ammonium sulfate to about 3 M ammonium sulfate and in some embodiments comprises 2.4 M ammonium sulfate and 10 mM Tris-HCl at about pH 8. In some embodiments, the conductivity of the equilibration/wash solution is from about 240 mS/cm to about 260 mS/cm. In some embodiments, the conductivity of the equilibration/wash solution is from about 240 mS/cm to about 300 mS/cm, in some embodiments and equilibration/wash solution is from about 250 mS/cm to about 270 mS/cm, and in some embodiments the equilibration/wash solution is from about 245 mS/cm to about 255 mS/cm. In some embodiments, a HIC column employed may be a column that is packed with resin Toyopearl butyl resin 650M (Tosoh Bioscience LLC, Montgomeryville, Pa.). In some embodiments, the column may be equilibrated with a solution comprised of about 1.5 M ammonium sulfate to about 3.0 M ammonium sulfate. In some embodiments, the column may be equilibrated with a solution comprised of 2.5 M ammonium sulfate and 10 mM Tris-HCl.

Hydrophobic interaction membranes may be any such membrane that binds either biologically active molecules of interest or impurities based primarily on hydrophobic interactions. Examples of HIC membranes include, but are be limited to Pall supor polyethersulfone ("PES") filters, PVDF filters, GE PES capsule filters, and similar hydrophilic membranes with low protein binding and broad chemical compatibility. Typical HIC resins include, but not limited to butyl, hexyl, phenyl, octyl, propyl, neopentyl, hydroxypropyl, benzyl, methyl and derivatives thereof.

In some embodiments, the ion exchange eluate may be conditioned by diluting it with 3 M or 4.1 M ammonium sulfate to bring up the conductivity between from about 240 mS/cm to about 290 mS/cm, and in some embodiments, from about 245 mS/cm to about 255 mS/cm. When using HIC method I, the diluted ion exchange eluate may flow through the conditioned HIC cartridge, at a flow rate, in some embodiments, of from about 100 mL/min to about 200 mL/min. The flow-through may be collected for subsequent ultrafiltration/diafiltration. Optionally, the HIC cartridge may be washed with water, and the wash solution recovered to analyze the contaminants removed from the product. When using method II, the diluted ion exchange eluate may be loaded to the column at the flow rate 10-20 bed volume/minute (BV/min). The biologically active molecule of interest may be washed, such as from about 1.0 M ammonium sulfate to about 2.5 M ammonium sulfate until the absorbance returns to baseline, then eluted with for example 0.5 to 2.0 M ammonium sulfate. The impurities may be stripped with sterile water for injection (WFI) so that the column can be regenerated for repeatable use. Method III uses a HIC membrane as described in method I, followed by HIC column as described in method II. The choice for method I, II or III is dependent on the product property and quality requirements, which can be determined by one skilled in the art. Using any HIC method, an HIC eluate is generated which contains the biologically active material of interest. Those of skill in the art will recognize that flow rates can be easily increased by using large membrane areas or column diameters and that the specific salts concentrations of the solutions listed can be altered to maximize the yield and purity of specific biomolecules using no more than ordinary experimentation.

Optionally, the biologically active material of interest, which is present in the HIC eluate, may be further purified. In some embodiments, the HIC eluate may be subjected to ultrafiltration/diafiltration to concentrate the biologically active material of interest, remove excess salts, and if desired, change the composition of the diluent. Methods for performing ultrafiltration/diafiltration are well known to those of skill in the art. In some embodiments, tangential flow filtration is used. In some embodiments, batch methods are used.

Ultrafiltration/diafiltration membranes may be selected based on nominal molecular weight cut-off ("NMWCO") so as to retain the biologically active material of interest in the retentate, while allowing low molecular weight materials such as salts to pass into the filtrated. One skilled in the art will be able to select such membranes based on the size and nature of the product of interest, coupled with no more than ordinary experimentation. In some embodiments, such as some embodiments when the biologically active material of interest is a plasmid, ultrafiltration/diafiltration may be performed using either a Pall Centramate unit (Pall Corporation, East Hills, N.Y.) or Millipore Pellicon® XL unit (Millipore Corporate, Billerica, Mass.) or an unit with similar characteristics, and the membranes used may be either Pall Omega™ suspended screen membrane cassettes (Pall Corporation, East Hills, N.Y.) or Millipore medium screen membrane cassettes (Millipore Corporate, Billerica, Mass.) or a similar cassette known in the art with a NMWCO of 100 kD or 50 kD. In some embodiments, plasmid may be concentrated to at least about 2.5 mg/mL, in some embodiments to at least about 5.0 mg/mL, in some embodiments to at least about 10.0 mg/mL, while in other embodiments the concentration is at least 12.5 mg/mL, and in other embodiments the concentration is at least 15 mg/mL or more. In some embodiments, the conductivity of the concentrated plasmid solution is less than about 50 mS/cm.

Concentrated desalted biologically active material of interest recovered in the retentate from the ultrafiltration/diafiltration may optionally be subjected to sterile filtration, if a sterile product is desired. Methods for sterile filtration are well known to those of skilled in the art, and any such method may be selected. The resulting material consists of substantially purified biologically active product. The product may be used for a variety of purposes, including, but not limited to, pharmaceutical, veterinary, or agricultural applications. Thus, the methods provide for a bulk preparation of substantially purified, biologically active molecules. These molecules may be plasmids. In some embodiments, they may be plasmids that are substantially free of genomic DNA, RNA, protein and endotoxin.

In some embodiments, such as the embodiments where the biologically active molecule is a plasmid, sterile filtration may preferably be performed using a Pall AcroPak™ 200 filter (Pall Corporation, East Hills, N.Y.) with a 0.22 μm cut-off.

The plasmid DNA produced by the process provided has shown a high purity and extremely low contaminations. In some embodiments, the high purity of plasmid DNA is plasmid DNA being present at levels greater than or equal to 90%, greater than or equal to 91%, greater than or equal to 92%, greater than or equal to 93%, greater than or equal to 94%, greater than or equal to 95%, greater than or equal to 96%, greater than or equal to 97%, greater than or equal to 98%, or greater than or equal to 99%. It is readily apparent that purity can be characterized by a low level of contaminants, including low levels of RNA, genomic DNA, endotoxin, and protein. In some embodiments, the plasmid DNA may be in quantities of about 10 mg or more, 20 mg or more, 30 mg or more, 100 mg or more, 200 mg or more, 300 mg or more, 500 g or more, 1 g or more, 10 g or more, 20 g or more, 30 g or more, 100 g or more, 200 g or more, 300 g or more, 1 kg or more, or 2 kg or more. In some embodiments, the plasmid DNA may be in a concentration 1 mg/mL or more FIG. 1 shows a schematic of one embodiment of the manufacturing process.

The embodiment shows a continuous process that is used to take a given sample of cells and have same undergo steps of purification processes starting from beginning, including lysis and neutralization steps, up until the separation steps (i.e., start of ion-exchange chromatography) in a continuous flow of sample. The cells are resuspended in resuspension solution contained in a cell suspension tank 101. The lysis solution is contained in a lysis solution tank 102. The cell suspension and lysis solution are pumped into the two inlets of an "Y" connector with pump 104 or 105, respectively. The solution exiting the "Y" connector was mixed by a high shear, in-line mixer 107. The lysate solution exiting the mixer 107 passes through a holding coil 108 for an holding period of 4-6 minutes. The lysis solution/cell mixture exiting the holding coil enters a bubble column mixer 109 while simultaneously a pump 106 delivers neutralization/precipitation (NP) solution from another tank, NP solution tank 103, into the bubble column mixer. Simultaneously, compressed gas from compressed gas tank 110, is fed into the sparger which is located at the bottom of the bubble column mixer 109. The neutralized lysate solution is collected in a container 111. The lysate solution is simultaneously processed by the following process after a period of 1-60 minutes of collecting the lysate in the container 111. A pump for primary filtration 112 delivers the crude lysate solution through a primary filter 113. The primary filtered solution after filter 113 is simultaneously pumped into a secondary filter 115 via pump 114. The filtered solution resulting from 115 is filtered through a third filter 117 via pump 116. A pump for clarified lysate 118 drives flow from a container for clarified lysate 119 to a mixer 121, which mixes with water from water tank 120. The mixed and diluted solution is collected in a container for diluted lysate 122. Diluted neutralized lysate solution is pumped to pre-conditioned Mustang® Q cartridge 124, which is accomplished by pump 123.

In some embodiments, the product of the process provided herein is a purified, concentrated, desalted, sterile-filtered plasmid can be substantially free of impurities such as protein, genomic DNA, RNA, and endotoxin. Low levels of these impurities or contaminants, preferably substantial free amounts, are provided herein, with the most preferred levels being undetectable amounts of such impurities or contaminants. In some embodiments, the residual protein, as determined by BCA (bicinchoninic acid) Protein assay (Pierce Biotechnology, Inc., Rockford, Ill.), in the solution of biologically active molecule, preferably plasmid, produced by provided production methods may be less than or equal to about 1% (by weight), less than or equal to 0.9%, less than or equal to 0.8%, less than or equal to 0.7%, less than or equal to 0.6%, less than or equal to 0.5%, less than or equal to 0.4%, less than or equal to 0.3%, less than or equal to 0.2%, or less than or equal to about 0.1%. In some embodiments, the residual protein is less than or equal to 0.2% and, more preferably, less than or equal to 0.1%. In some embodiments, the residual endotoxin in the solution of biologically active molecule, preferably plasmid, produced by provided production methods may be less than about 100 endotoxin units per milligram of plasmid (EU/mg), less than about or equal to about 20 EU/mg, less than about or equal to about 10 EU/mg, less than or equal to about 1.0 EU/mg, less than or equal to about 0.9 EU/mg, less than or equal to about 0.8 EU/mg, less than or equal to about 0.7 EU/mg, less than or equal to about 0.6 EU/mg, less than or equal to about 0.5 EU/mg, less than or equal to about 0.4 EU/mg, less than or equal to about 0.3 EU/mg, less than or equal to about 0.2 EU/mg, or less than or equal to about 0.1 EU/mg. Preferably, in some embodiments, the endotoxin level is less than or equal to about 0.2 EU/mg, and more preferably, less than or equal to about 0.1 EU/mg. In some embodiments, residual RNA, as determined by hydrophobic interaction HPLC, in the solution of biologically active molecule, preferably plasmid, produced by provided production methods may be less than or equal to about 5% (by weight), less than or equal to about 1%, less than or equal to 0.9%, less than or equal to 0.8%, less than or equal to 0.7%, less than or equal to 0.6%, less than or equal to 0.5%, less than or equal to 0.4%, less than or equal to 0.3%, less than or equal to 0.2%, or less than or equal to about 0.1%. Preferably, in some embodiments, the amount of RNA is less than or equal to about 0.5%, and more preferably, less than or equal to about 0.4%. In some embodiments, residual genomic DNA, as determined by qPCR, in the solution of biologically active molecule, preferably plasmid, produced by provided production methods may be less than or equal to about 5% (by weight), less than or equal to about 1%, less than or equal to 0.9%, less than or equal to 0.8%, less than or equal to 0.7%, less than or equal to 0.6%, less than or equal to 0.5%, less than or equal to 0.4%, less than or equal to 0.3%, less than or equal to 0.2%, less than or equal to about 0.1%, less than or equal to about 0.01%, less than or equal to about 0.001%, less than or equal to about 0.0001%, less than or equal to about 0.00001%, or less than or equal to about 0.000001%. Preferably, in some embodiments, the amount of genomic DNA is less than or equal to about 0.1%, and more preferably less than about 0.001%, and most preferably less than or equal to about 0.000001%.

Large quantities of plasmid DNA in high yields and at high concentrations can be produced by the methods provided herein. The plasmid DNA produced by the process provided include solutions of plasmid DNA of high purity. In some embodiments, the high purity of plasmid DNA is greater than or equal to about 90%, greater than or equal to about 91%, greater than or equal to about 92%, greater than or equal to about 93%, greater than or equal to about 94%, greater than or equal to about 95%, 5 mg/mL or more, 6 mg/mL or more, 7 mg/mL or more, 8 mg/mL or more, 9 mg/mL or more, 10 mg/mL or more, 11 mg/mL or more, 12 mg/mL or more, 13 mg/mL or more, 14 mg/mL or more, 15 mg/mL or more. In some embodiments, the plasmid DNA may be in a concentration from about 5 mg/mL to about 15 mg/mL, from about 5 mg/mL to about 14 mg/mL, from about 5 mg/mL to about 13 mg/mL, from about 5 mg/mL to about 12 mg/mL, from about 5 mg/mL to about 11 mg/mL, from about 5 mg/mL to about 10 mg/mL, from about 5 mg/mL to about 9 mg/mL, from about 5 mg/mL to about 8 mg/mL, a concentration from about 6 mg/mL to about 15 mg/mL, from about 6 mg/mL to about 14 mg/mL, from about 6 mg/mL to about 13 mg/mL, from about 6 mg/mL to about 12 mg/mL, from about 6 mg/mL to about 11 mg/mL, from about 6 mg/mL to about 10 mg/mL, from about 6 mg/mL to about 9 mg/mL, from about 6 mg/mL to about 8 mg/mL, a concentration from about 7 mg/mL to about 15 mg/mL, from about 7 mg/mL to about 14 mg/mL, from about 7 mg/mL to about 13 mg/mL, from about 7 mg/mL to about 12 mg/mL, from about 7 mg/mL to about 11 mg/mL, from about 7 mg/mL to about 10 mg/mL, from about 7 mg/mL to about 9 mg/mL, from about 8 mg/mL to about 15 mg/mL, from about 8 mg/mL to about 14 mg/mL, from about 8 mg/mL to about 13 mg/mL, from about 8 mg/mL to about 12 mg/mL, from about 8 mg/mL to about 11 mg/mL, from about 8 mg/mL to about 10 mg/mL, from about 9 mg/mL to about 15 mg/mL, from about 9 mg/mL to about 14 mg/mL, from about 9 mg/mL to about 13 mg/mL, from about 9 mg/mL to about 12 mg/mL, from about 9 mg/mL to about 11 mg/mL, from about 10 mg/mL to about 15 mg/mL, from about 10 mg/mL to about 14 mg/mL, from about 10 mg/mL to about 13 mg/mL, from about 10 mg/mL to about 12 mg/mL, from about 11 mg/mL to about 15 mg/mL, from about 11 mg/mL to about 14 mg/mL, from about 11 mg/mL to about 13 mg/mL, from about 12 mg/mL to about 15 mg/mL, from about 12 mg/mL to about 14 mg/mL, or from about 13 mg/mL to about 15 mg/mL. In some embodiments, the plasmid DNA may be in such concentration as set forth with a percent of supercoiled of greater than about 50%, 55%, 60%, 65%, 70%, 75%, 80%, 81%, 82%, 83%, 84%, 85%, 86%, 87%, 88%, 89%, 90%, 91%, 92%, 93%, 94% or 95% supercoiled plasmid, and preferably greater 80% supercoiled plasmid. In some embodiments, the plasmid DNA may be in such concentration as set forth with a percent of supercoiled of 50-90%, 50-80%, 50-75%, 50-70%, 50-65%, 50-60%, 60-90%, 60-80%, 60-75%, 60-70%, 65-90%, 65-80%, 65-75%, 65-70%, 70-90%, 70-80%, 70-75%, 80-90%, 85-90%, 90-95%, or more. In some embodiments, the plasmid DNA may be in such concentration as set forth with a percent of supercoiled and relaxed (open circle non-degraded) of 90% or more, 95% or more, or 98% or more. In some embodiments, the plasmid DNA may be in such concentration as set forth with a percent of supercoiled of 50% or more with essentially the remainder as relaxed (open circle non-degraded) plasmid after storage for 2 years or more, 60% or more with essentially the remainder as relaxed (open circle non-degraded) plasmid after storage for 2 years or more, 65% or more with essentially the remainder as relaxed (open circle non-degraded) plasmid after storage for 2 years or more, 85% or more with essentially the remainder as relaxed (open circle non-degraded) plasmid after storage for 2 years or more, wherein the storage below the freezing point of water. In some embodiments, the plasmid DNA may be in such concentration as set forth with a percent of supercoiled and relaxed (open circle non-degraded) of 90% or more, 95% or more, 98% or more after storage for 2 years or more, wherein the storage is below the freezing point of water. Such plasmid preparations as described herein may be produced as products by the processes described herein.

EXAMPLES

The present invention is further illustrated in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

*Escherichia coli* ("*E. coli*") cells containing a plasmid A were fermented to high density of an optical cell density ("$OD_{600}$") at 72 when harvested by centrifugation. Plasmid A has a size of 6549 bp. The plasmid typically replicates at a low copy number of ~250 copies/cell. Approximately 3.1 kg wet cell weight ("WCW") of cell paste was suspended in a resuspension buffer consisting of 25 mM Tris-hydrochloride ("Tris-HCl", J.T. Baker, Phillipsburg, N.J.), 10 mM edetate disodium ("$Na_2EDTA$", Fisher Scientific, Fair Lawn, N.J.), pH 8, to a final volume of approximately 21.5 L. This cell suspension was pumped at 300 mL/min into one side of a "Y" connector. Simultaneously, lysis solution consisting of 0.2 N sodium hydroxide ("NaOH", J.T. Baker, Phillipsburg, N.J.), 1% sodium dodecyl sulfate ("SDS", J.T. Baker, Phillipsburg, N.J.) was pumped at 300 mL/min into the other side of the "Y" connector. The combined fluids exiting the "Y" connector were immediately passed through a Silverson Model L4R rotor/stator mixer fitted with a standard Emulsor Screen (Silverson Machines, Inc. East Longmeadow, Mass.) and an in-line assembly. The mixer was operated at a rotor speed of 800 rpm.

The fluid exiting the rotor/stator mixer was passed through a 50-foot, 0.625 inch (internal diameter) holding coil. At a total flow rate of approximately 600 mL/min, transit time through the holding coil was approximately 5 minutes to allow for complete cell lysis.

Cell lysate (lysate solution) exiting the holding coil was passed into a bubble column mixer. Simultaneously, cold (approximately 4° C.) neutralization/precipitation solution consisting of 1 M potassium acetate (J.T. Baker, Phillipsburg, N.J.), 7 M ammonium acetate (EMD Chemicals, Inc., Bibbstown, N.J.) was independently pumped into the bubble column mixer at 600 mL/min. The lysate solution and neutralization/precipitation solutions were flowed vertically up the mixing column and through the outlet near the top. While the solutions passed through the mixing column, compressed air was introduced into the bottom of the column at a rate of approximately 3.0 slpm through a sintered sparger designed to provide a constant stream of fine bubbles throughout the diameter of the mixing. Excess air was vented through the top of the column. As the lysate solution and neutralization/precipitation solutions passed through the column, they were continuously mixed by the gentle turbulence of the rising bubbles. This was evidenced by the formation of a white, flocculent precipitate (debris components) consisting of potassium SDS, denatured cellular proteins, bound lipids and cell wall components, and associated genomic DNA.

The neutralized precipitated lysate (dispersion of neutralized lysate solution and debris) exiting the bubble column mixer was collected in a settling container. This process was operated in a continuous mode until the entire suspension of cell paste had been lysed, neutralized and precipitated, and collected in the settling tank. Total solution volumes were 21.5 L of cell suspension plus a 5 L wash of the resuspension tank with resuspension buffer, 26.5 L of lysis solution, and 53 L of neutralization solution, for a total volume of approximately 106 L.

After collection, the material in the settling tank was observed through a sight glass. The flocculent precipitate could be seen rising to the surface of the liquid, aided by clearly visible air bubbles that were entrapped in the solids. A vacuum of approximately 28 in·Hg was applied to the settling tank, leading to significant and visible compaction of the floating precipitate.

The material was held under vacuum in the settling tank at room temperature for approximately 16 hours. The vacuum was then slowly vented to avoid disrupting the compacted precipitate. The plasmid-containing liquor (neutralized lysate solution) was carefully pumped from the tank through a sanitary fitting at the bottom. The liquid and precipitate levels in the tank were continuously monitored, and pumping was halted in time to ensure that the precipitate did not exit the tank. This was subjected to a 10 μm depth filtration, followed by 0.1 μm final filtration. A portion of the neutralized lysate solution was lost during filtration, due to clogging of the filters. As a result, approximately 69 L of cleared neutralized lysate solution was obtained. The neutralized lysate solution was then diluted with approximately 93 L of purified water achieving a total volume of 162 L and approx. conductivity of 97 mS/cm, in preparation for further processing with anion exchange. Plasmid concentration in the filtered neutralized lysate solution was estimated to be about 17 μg/mL, corresponding to approximately 1170 mg of total plasmid.

The cleared, diluted neutralized lysate solution was further purified by anion exchange. A 260 mL bed volume Pall Mustang Q cartridge was equilibrated with 4 L of 0.67 M Sodium Chloride ("NaCl", J.T. Baker, Phillipsburg, N.J.) in 1×Tris-EDTA ("TE") buffer composed of 10 mM Tris-HCl (J.T. Baker, Phillipsburg, N.J.) and 1 mM EDTA (Fisher Scientific, Fair Lawn, N.J.) at pH 8. The volume of 162 L of diluted neutralized lysate solution was pumped onto the Q cartridge at a flow rate of 1.2 L/min. Ultraviolet ("UV") absorbance of the cartridge effluent at 260 nm was monitored and recorded using a strip-chart recorder. After loading, the cartridge was washed with equilibration buffer at 1.2

L/min until the $A_{260}$ of the effluent approached baseline. Plasmid was then eluted from the cartridge with 1×TE buffer containing 1 M NaCl (J.T. Baker, Phillipsburg, N.J.), pumped at 1.2 L/min. Elution was terminated with the $A_{260}$ returned to baseline. Total eluate volume was approximately 4.8 L and contained a total of approx. 915 mg of DNA based on $A_{260}$. The yield of the Q anion exchange is approximately 78%. Contaminants including protein, the majority of RNA, genomic DNA and endotoxin were removed in the flow through and wash at this step.

The Q eluate was further purified by hydrophobic interaction via method II of butyl column. A K5/15 Amersham (Piscataway, N.J.) column was packed with 290 mL bed volume ("By") of Toyopearl butyl resin 650M (Tosoh Bioscience LLC, Montgomeryville, Pa.). A volume of 24 L 3 M ammonium sulfate (EMD Chemicals, Inc., Gibbstown, N.J.) was mixed with 4.8 L Q elute before loading. The column was equilibrated with 2 L of 2.5 M ammonium sulfate (EMD Chemicals, Inc., Gibbstown, N.J.), pumped at 43 mL/min. The conditioned Q eluate was loaded to the butyl column at 43 mL/min, followed by washing with 5 L of 2.5 M ammonium sulfate (EMD Chemicals, Inc., Gibbstown, N.J.) at 43 mL/min, and the product was eluted with 1.5 L of 1.8 M ammonium sulfate (EMD Chemicals, Inc., Gibbstown, N.J.) at 43 mL/min. The column was stripped with sterile water for injection ("WFI", Baxter Healthcare, Deerfield, Ill.) to remove bound contaminants including RNA and endotoxin, and was regenerated for repeatable use. The eluate achieved approx. 870 mg of plasmid with the yield of 95%, while the supercoiled percentage of plasmid was enriched from 66% after Q to more than 80% after the butyl column step.

The eluate from butyl HIC was concentrated and desalted by ultrafiltration/diafiltration ("UF/DF"), using a Pall Centramate™ cassette holder fitted with one Pall Omega suspended screen membrane cassettes (Pall Corporation, East Hills, N.Y.), with an area of 1 $ft^2$ and a nominal molecular weight cut-off of 50 kDa. A volume of 41.2 mL of bulk retentate was recovered, with a DNA concentration of 9.026 mg/mL (by $A_{260}$). First wash of WFI for the UF/DF rig yielded 46.9 mL with the concentration of 1.6 mg/mL. Second wash of WFI yielded 65.8 mL with the concentration of 0.268 mg/mL. Combined DNA recovery after UF was approximately 47 6 mg with the yield of 55%. The final supercoiled percentage of plasmid achieved was more than 87% after UF.

Samples from EXAMPLE 1 were subjected to analysis by agarose gel electrophoresis, which is displayed as FIG. 2. Three major bands are present in all sample lanes (lane 2-5), while the lowest band is the supercoiled format of target plasmid A (6.5 kb). Lane 1 represents the supercoiled plasmid ladder (Invitrogen). Lane 2 represents the cell lysate containing a 6.5 kb plasmid product, while a large amount of RNA was also present in the sample. Lane 3 represents the product after Q anion exchange, which showed that the plasmid was concentrated with less RNA. Lane 4 displayed the product after purification with hydrophobic interaction, and lane 5 represents final product blended after UF. The contaminant RNA in the lysate was removed and the purity of the desired supercoiled plasmid was substantially increased from 60% to >85%.

Example 2

An amount of 3140 gram *E. coli* cells containing plasmid B was resuspended in resuspension buffer consisting of 25 mM Tris-HCl (J.T. Baker, Phillipsburg, N.J.) at the pH of 8 and 10 mM $Na_2EDTA$, to a final volume of 18.8 L. Plasmid B has a size of 4.7 kb. The resuspended cells were mixed with the lysis solution consisting of 0.2 N NaOH (J.T. Baker, Phillipsburg, N.J.) and 1% SDS (J.T. Baker, Phillipsburg, N.J.) at an equal flow rate of 300 mL/min by a Silverson Model L4R rotor/stator mixer, which was operated at a rotor speed of 800 rpm. The lysate effluent from mixer retained 5-minute holding time in the holding coil before entering the bubble column to mix with the pre-chilled (4-5° C.) neutralization/precipitation (NP) solution. The NP solution containing 1 M potassium acetate (J.T. Baker, Phillipsburg, N.J.) and 3 M ammonium acetate (EMD Chemicals, Inc., Bibbstown, N.J.) was fed to the bubble column mixer at 600 mL/min, simultaneously, the compressed air was introduced from the bottom sparger at a flow rate of 3-5 slpm.

The neutralized cell lysate was first received by a woven mesh bag of 200-400 μm hanging below the outlet port of the bubble column. Large cell flocculent was retained in the bag, whereas the crude lysate solution containing the plasmid DNA and reduced cell debris was collected in the pre-chilled (5° C.) settling tank. Simultaneously, the generated crude lysate was pumped to a 48 μm pleated cartridge filter (CPI filters, Houston, Tex.) fitted in an ECOLINE filter vessel (Eaton Filtration, Iselin, N.J.) at a flow rate of 2 L/min. The primary filtered lysate was collected in a container with a total volume of 75 L recovered. A second filtration was performed afterwards. The primary filtered lysate was pumped to a 523 multi-layer bag filter (Knight Corporation, Barrington, Ill.) fitted in an ECOLINE filter vessel (Eaton Filtration, Iselin, N.J.) at a flow rate of 2 L/min. The recovered solution was collected in a container with total volume of 65 L recovered. Finally, a depth filtration was conducted with Millistak Pod disposable depth filter system (Millipore, Billerica, Mass.). The filter media had a pore size distribution of 0.2-2.5 μm. A Pod filter with the membrane area of 0.11 $m^2$ was used to clarify the secondary filtered lysate at a flow rate of 0.5 L/min. A volume of 60 L final clarified lysate was achieved, which demonstrated a high clarity of NTU value lower than 2. The plasmid purity and forms in the lysate samples at each stage of filtration were indistinguishable.

Example 3

*E. coli* cells containing a plasmid C (plasmid size of 3.5 kb) were fermented to high cell density and harvested by centrifugation. A wet cell weight of 24.4 kg cells were recovered from 400-L working volume of fermentation. The cells were resuspended with 171 L of resuspension buffer consisting of 25 mM Tris-HCl (J.T. Baker, Phillipsburg, N.J.) at the pH of 8 and 10 mM $Na_2EDTA$ (Mallinckrodt Baker, Phillipsburg, N.J.) for a period of 3 hours. The resuspended cells were mixed with fresh lysis solution by Silverson high shear mixer at the same flow rate of 600 ml/min, and held for approximately 5 min accomplished by a holding loop. The neutralization/precipitation solution consisting of 1 M potassium acetate (J.T. Baker, Phillipsburg, N.J.) and 3 M ammonium acetate (EMD Chemicals, Inc., Bibbstown, N.J.) were pumped to the bubble mixer at a flow rate of 1.2 L/min to mix with lysed cells. Compressed air fed at a gas flow rate of 5-6 slpm served as the mixing force and transporting the neutralized lysate to a collecting tank. An approximate period of 5 hour was used for the lysis process. The neutralized cells exiting the bubble mixing device were diverted to a collecting tank and subject to following filtration continuously.

The neutralized crude lysate was processed with three sequential filtrations upon its generation and these clarification processes were operated simultaneously with the lysis process. The initial filtration was performed by pumping the crude lysate containing cell flocculents into a TOPLINE filter vessel (Eaton Filtration, Iselin, N.J.) fitted with a 48 µm pleated cartridge filter (CPI filters, Houston, Tex.) at a flow rate of 2.4 L/min. The primary filtration was employed to remove the majority of large particles such as cell floccs, and a pleated membrane offers more filtration area, thus higher flow rate and larger process capacity than a single layer or multi-layer construct. Four pleated cartridges were used to process a volume of 680 L neutralized crude lysate containing cell floccs, while recovered primary filtered lysate was estimated at 600 L. The solution exiting the 48 µm pleated cartridge filter was directly pumped to a secondary ECOLINE filter vessel (Eaton Filtration, Iselin, N.J.) fitted with a 1 µm multi-layer cartridge filter (CPI filters, Houston, Tex.) at a flow rate of 2.4 L/min. This step removed a majority of small particles ranged between 1 µm and 50 µm in the secondary filtered lysate. The subsequent Mustang Q has a pore size equivalent to 0.2 µm, and thus a third depth filtration by a filter with the absolute based pore size of 0.2 µm or lower was performed. The depth filter Millitak+Pod filter system is able to achieve both large process volume and a high retention to fine particles. The Millistak C0HC filter (Millipore, Billerica, Mass.) fitted in a stainless steel Pod holder was used to reduce the turbidity of lysate to 2 Nephelometric Turbidity Unit (NTU). A membrane area of 1.1 $m^2$ C0HC filter processed a volume of 400 L secondary filtered lysate.

The filtered lysate exiting Millistak filter was collected in a container. A fraction of solution from this container was pumped to a "Y" connector at a flow rate of 2.2 L/min to mix with water which was pumped to the same "Y" connector at a flow rate of 0.7 L/min. The mixture was flowed into a Kenics in-line mixer leading into another holding tank. The conductivity of such diluted lysate in the holding tank had a range of 90-95 mS/cm. A volume of 400 L diluted lysate was loaded to a 10 inch Mustang Q (Pall, East Hills, N.Y.) which had a bed volume of 260 ml. The Q capsule was saturated before 200 L of Q load. An approximate 3 g of plasmid DNA was recovered in the Q eluate. The supercoiled percentage of Q product was between 80%-90%, and the RNA content in the Q eluates was not noticeable by gel analysis.

Figure 3:
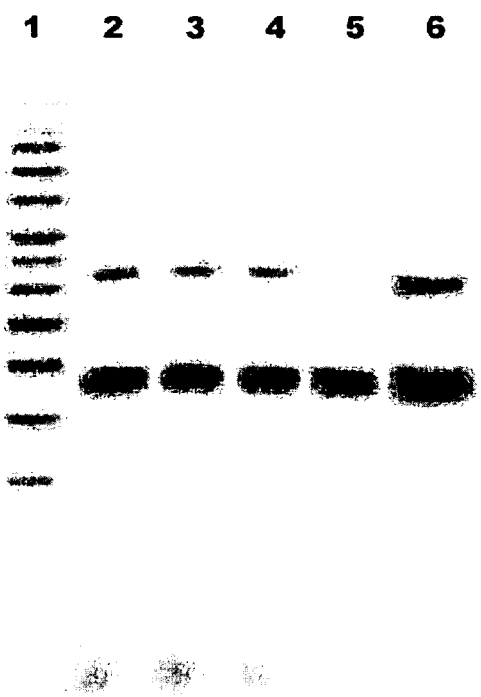
FIG. 3 displays a picture of an electrophoretic gel that includes samples from EXAMPLE 3. Lane 1 represents the supercoiled plasmid ladder (Invitrogen); Lane 2 represents the lysate after primary filtration using a 48 µm pleated cartridge; Lane 3 represents the filtrate after secondary filtration using a 1 µm pleated cartridge; Lane 4 represents the filtrate after a third filtration using a C0HC Pod filter; Lane 5 represents the eluate product fraction #1 after undergoing step of Mustang Q anion exchange; and Lane 6 represents the secondary fraction of Q eluate.

Samples from EXAMPLE 3 were subjected to analysis by agarose gel electrophoresis, which is displayed in FIG. 3. The band of the highest intensity in each lane represents the supercoiled (SC) form of plasmid, which is present at a percentage ranging between 80-90%. Lane 1 represents the supercoiled plasmid ladder (Invitrogen). Lane 2 represents the lysate after primary filtration using a 48 µm pleated cartridge, and shows a high RNA content. Lane 3 represents the filtrate after secondary filtration using a 1 µm pleated cartridge, and also shows a high RNA content. Lane 4 represents the filtrate after a third filtration using a C0HC Pod filter, and shows a reduced RNA ratio. Lane 5 represents the eluate product fraction #1 after undergoing step of Mustang Q anion exchange, which demonstrated a high purity with limited RNA. Lane 6 represents the secondary fraction of Q eluate, with similar purity to eluate #1.

Example 4

A wet cell weight of 25 kg of *E. coli* cells containing plasmid C was resuspended in 105 L of resuspension buffer consisting of 25 mM Tris-HCl (J.T. Baker, Phillipsburg, N.J.) at the pH of 8 and 10 mM $Na_2EDTA$, for a total period of 3 hours. Plasmid C has a size of 3.5 kb. The resuspended cells were pumped to a Silverson Model L4R rotor/stator mixer at a flow rate of 1500 ml/min, simultaneously, the lysis solution consisting of 0.2 N NaOH (J.T. Baker, Phillipsburg, N.J.) and 1% SDS (J.T. Baker, Phillipsburg, N.J.) was delivered to the same mixer at a flow rate of 1500 ml/min. The mixture containing lysed cells passages through a holding coil with the inner diameter (ID) of 1 inch and length of 100 feet. The approximate retention time was 5 minutes for the lysate from entering the mixer until exiting the holding coil. The lysed cells then entered the bubble column to be in contact with the pre-chilled (4-5° C.) neutralization/precipitation (NP) solution. The NP solution containing 1 M potassium acetate (J.T. Baker, Phillipsburg, N.J.) and 3 M ammonium acetate (EMD Chemicals, Inc., Bibbstown, N.J.) was fed to the bubble column mixer at 3000 mL/min. Simultaneously, compressed air was introduced from the bottom sparger at a flow rate of 6-10 slpm to serve as the mixing force and facilitate the neutralized solution into a diverting pipe directing to a crude lysate tank.

After collecting the crude lysate for a period of 20 minutes, the solution was pumped from the bottom of crude lysate tank to a TOPLINE filter vessel (Eaton Filtration, Iselin, N.J.) fitted with a 48 µm pleated cartridge filter (CPI filters, Houston, Tex.) at a flow rate of 6 L/min. Simultaneously, the filtrate from primary filter vessel was pumped to a secondary TOPLINE filter vessel (Eaton Filtration, Iselin, N.J.) fitted with a 1 µm pleated cartridge filter (CPI filters, Houston, Tex.) at a flow rate of 6 L/min. The primary filtration removed 99% of particles greater than 48 µm, and five of 10 inch cartridge filters clarified the total volume of 700 L of crude lysate. Use of three 10 inch 1 µm cartridge filters enabled the completion of secondary filtration to remove 99% of particles greater than 1 µm. The filtrate from the secondary vessel was collected in a clarified lysate tank with the aid of a pump at a flow rate of 5-6 L/min. A third filter system of Millitak+C0HC Pod filter (Millipore, Billerica, Mass.) fitted in a stainless steel pilot scale Pod holder was employed to achieve a high clarity for subsequent Mustang Q purification. The solution from the clarified lysate tank was pumped to the pod filter at a flow rate of 6 L/min. A membrane area of 2.2 $m^2$ C0HC filter processed a volume of 650 L secondary filtered lysate before the inlet pressure reached 10 psi. The filtrate by the third Pod filter was collected in the filtered lysate container.

The filtered lysate was delivered to a "Y" connector and mix with water at a ratio of 0.3-0.4 V water/V lysate via a Kenics in-line mixer before loading to a Mustang Q. The lysate was pumped at a flow rate of 5 L/min, while the water was fed at a flow rate of 1.75-2 L/min. The mixture was collected in the diluted lysate tank. The conductivity of such diluted lysate in the holding tank had a range of 90-95 mS/cm. An approximate volume of 800 L diluted lysate was loaded to a Mustang Q XT5000 (Pall, East Hills, N.Y.) which had a bed volume of 5000 ml. An approximate 25 g of plasmid DNA was recovered in the Q eluate. The recovered Q eluate exhibited high percentage of supercoiled form and limited levels of contaminations.

Example 5

The following table I represents fourteen plasmid preparations produced using Method II with plasmid A, a low copy plasmid, and some purity parameters detected therein. The protocols for production were that discussed in Example 3, above.

Analysis of Plasmid Samples

Plasmid C has a size of 3.5 kb (as in Example 3 and Example 4). Plasmid D1-D3 ranges from 4.4-4.7 kb, having similar construct except of expression genes. Plasmid E1-E2 has a size of 3.8 kb, with similar construct other than expression genes. Plasmid F has a size of 2.5 kb.

TABLE I

| Assay | Units | Plasmid C Lot #1 | Plasmid C Lot #2 | Plasmid C Lot #3 | Plasmid C Lot #4 | Plasmid D Lot #1 |
|---|---|---|---|---|---|---|
| Concentration by A260 | mg/mL | 2.5 | 2.5 | 2.4 | 3.0 | 4.4 |
| Host Cell RNA | % | 0.4 | 0.63 | 0.31 | 0.62 | ≤0.1 |
| Host Cell Protein | % | ≤0.1 | ≤0.12 | ≤0.13 | ≤0.1 | ≤0.07 |
| Host Cell DNA | % | 0.0000002 | ≤0.000002 | ≤0.000002 | ≤0.000002 | ≤0.0000003 |
| Endotoxin | EU/mg | 1 | 3.76 | ≤1.25 | 1.383 | 0.4 |
| pH | | 7.1 | 6.87 | 5.70 | 6.22 | 5.2 |
| Osmolality | mOsm/kg H2O | 19 | 19 | 11 | 15 | 15 |

| Assay | Units | Plasmid D1 Lot #1 | Plasmid D2 Lot #1 | Plasmid D3 Lot #1 | Plasmid E1 Lot #1 | Plasmid E2 Lot #1 |
|---|---|---|---|---|---|---|
| Concentration by A260 | mg/mL | 9.2 | 8.1 | 8.5 | 6.0 | 6.0 |
| Host Cell RNA | % | ≤0.06 | ≤0.08 | ≤0.07 | ≤0.1 | 1 |
| Host Cell Protein | % | ≤0.03 | ≤0.04 | ≤0.04 | ≤0.1 | ≤0.1 |
| Host Cell DNA | % | 0.00000005 | 0.00000005 | ≤0.0000005 | ≤0.0000000001 | ≤0.0000000001 |
| Endotoxin | EU/mg | 1.1 | 1.2 | 1.9 | ≤0.1 | ≤0.1 |
| pH | | 6.2 | 5.8 | 6.0 | 6.5 | 5.5 |
| Osmolarity | mOsm/kg H2O | 58 | 32 | 47 | 10 | 32 |

The invention claimed is:

1. A large scale process for producing high purity samples of at least one biologically active molecule of interest from a plurality of bacterial cells, comprising the steps of:
   a) producing a lysate solution by contacting a cell suspension of said plurality of bacterial cells with lysis solution;
   b) neutralizing said lysate solution with a neutralizing solution to produce a dispersion that comprises neutralized lysate solution and debris;
   c) filtering the dispersion through at least one filter to separate debris from the neutralized lysate solution;
   d) performing ion exchange separation on said neutralized lysate solution to produce an ion exchange eluate; and
   e) performing hydrophobic interaction separation on said ion exchange eluate to produce a hydrophobic interaction solution.

2. The method of claim 1, wherein step a) comprises mixing said cell suspension with lysis solution in a high shear, in-line mixer.

3. The method of claim 1, wherein step b) comprises mixing said lysate solution with said neutralizing solution in a bubble mixer.

4. The method of claim 1, wherein step e) comprises performing hydrophobic interaction separation using a hydrophobic interaction column or a hydrophobic interaction membrane to form a hydrophobic interaction solution.

5. The method of claim 1, further comprising the step:
   f) preparing a solution of at least one biologically active molecule by ultrafiltration of said hydrophobic interaction solution.

6. The method of claim 5, further comprising the step:
   g) preparing a sterile solution of at least one biologically active molecule by sterile filtration of said solution of biologically active molecules.

7. The method of claim 1, further comprising holding the dispersion for a period of time to separate the neutralized lysate solution from the debris and filtering the neutralized lysate solution through at least one filter.

8. The method of claim 1, wherein the producing step comprises contacting the cell suspension with the lysis solution in a mixer over a duration of from about 1 minutes to about 20 minutes.

9. The method of claim 8, wherein the duration is from about 4 minutes to about 8 minutes.

10. The method of claim 8, wherein the duration is about 5 minutes.

11. The method of claim 1, wherein said biologically active molecule is a plasmid.

12. The method of claim 1 wherein said ion exchange is an anion exchange membrane.

13. The method of claim 1, wherein step e) comprises performing hydrophobic interaction separation comprises butyl hydrophobic interaction chromatography in order to produce a hydrophobic interaction solution that is a butyl hydrophobic interaction chromatography solution eluate.

14. The method of claim 1, wherein the method comprises transitioning from one step to a subsequent step substantially continuously and comprises separating the neutralized lysate solution from the debris in the dispersion by collecting the lysate in a container and passing the dispersion through a primary filter to produce a first crude neutralized lysate solution.

15. The method of claim 14, further comprising passing the first crude neutralized lysate solution through a secondary filter to produce a subsequent crude neutralized lysate solution.

16. A large scale process for producing high purity samples of at least one biologically active molecule of interest from bacterial cells, comprising the steps of:
   contacting the bacterial cells in a dispersion of cells with lysis solution to form a lysate solution;

neutralizing the lysate solution by mixing a neutralization solution into the lysate solution with a bubble column mixer to form a neutralized mixture;

filtering the neutralized mixture through a primary filter and a secondary filter to form a filtered solution;

passing the filtered solution through an ion-exchange column to form a ion-exchange solution;

passing the ion-exchange solution through a hydrophobic interaction column or a hydrophobic interaction membrane to form a hydrophobic interaction solution; and ultrafiltration of the hydrophobic interaction solution to form a high purity sample of at least one biologically active molecules of interest;

wherein each transition from one step to a subsequent step in the large scale process from the contacting step to the passing the filtered solution step occur substantially continuously.

* * * * *